United States Patent [19]

Sheng

[11] 3,997,578
[45] Dec. 14, 1976

[54] OXIDATION OF ALCOHOLS TO CARBOXYLIC ACIDS WITH RUTHENIUM CATALYSTS AND PERACID OXIDIZING AGENTS

[75] Inventor: Ming Nan Sheng, Cherry Hill, N.J.

[73] Assignee: Atlantic Richfield Company, Los Angeles, Pa.

[22] Filed: May 12, 1975

[21] Appl. No.: 576,414

Related U.S. Application Data

[63] Continuation of Ser. No. 305,201, Nov. 9, 1972, abandoned.

[52] U.S. Cl. .......................... 260/413; 260/514 R; 260/514 H; 260/531 R; 260/537 P
[51] Int. Cl.² .................. C07C 51/26; C07C 51/28; C07C 51/24
[58] Field of Search ...................... 260/413, 531 R

[56] References Cited

UNITED STATES PATENTS

| | | | |
|---|---|---|---|
| 2,437,648 | 3/1948 | Milas | 260/413 |
| 3,479,403 | 11/1969 | MacLean | 260/530 R |
| 3,816,525 | 6/1974 | Schreyer | 260/413 |

FOREIGN PATENTS OR APPLICATIONS 938,932   10/1963   United Kingdom ........... 260/531 R

*Primary Examiner*—Patrick P. Garvin
*Assistant Examiner*—P. E. Konopka
*Attorney, Agent, or Firm*—Delbert E. McCaslin

[57] ABSTRACT

A process for the preparation of fatty acids by the oxidation of alcohols, particularly, primary alcohols, such as, octanol-1 and vicinal-diols, such as cyclohexane-1,2-diol, in which the alcohol is contacted with a peracid as an oxidizing agent in the presence of a ruthenium catalyst, such as, ruthenium chloride, ruthenium dioxide, etc., and an inert organic solvent, such as, heptane, hexane, chloroform, carbon tetrachloride, etc. If desired the process may include the addition of an organic or inorganic base, such as amines, and alkali metal and alkaline earth metal hydroxides, carbonates, phosphates, etc.

7 Claims, No Drawings

OXIDATION OF ALCOHOLS TO CARBOXYLIC ACIDS WITH RUTHENIUM CATALYSTS AND PERACID OXIDIZING AGENTS

This is a continuation, of application Ser. No. 305,201 filed Nov. 9, 1972, now abandoned.

BACKGROUND OF THE INVENTION

The present invention relates to a process for the catalytic oxidation of alcohols to produce carboxylic acids. More specifically, the present invention relates to a process for oxidizing primary alcohols and vicinal-diols to produce fatty acids in the presence of a ruthenium catalyst and a peracid oxidizing agent.

Fatty acids have heretofore been used commercially for the manufacture of synthetic lubricants and soaps. Consequently, the market for such fatty acids has generally exceeded the ability of industry to supply these materials from their natural sources. There is therefore a substantial demand for such fatty acids, particularly those having long carbon chains.

In the past, various processes have been developed for the production of fatty acids from various related materials. It has been proposed to treat various alcohols, such as, primary alcohols, with an oxidizing agent in the presence of a catalyst, such as ruthenium and a solvent to produce the corresponding fatty acids. For example, in Berkowitz, L. M. and Rylander, P. N., J. An. Chem. Soc. 80, p. 6682 (1958), it is reported that n-hexyl alcohol was oxidized with ruthenium tetroxide in carbon tetrachloride. This reaction was reported to produce about 10% of hexanoic acid as a product. In J. Org. Chem. Vol 33, p. 53 (1968), it was reported that a primary alcohol could be oxidized with excess sodium periodate in the presence of a catalytic amount of ruthenium dioxide in water. This particular reaction was reported to produce a 40% yield of the corresponding carboxylic acid. The House and Blankley reaction is reported to be as follows:

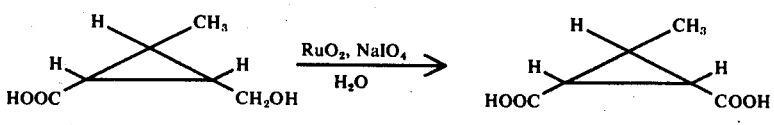

Obviously, the product yield in this particular instance was also extremely low when utilizing alcohols as a starting material and periodates as an oxidizing agent.

It is therefore an object of the present invention to provide a process for producing high yields of fatty acids from certain alcohols. Another and further object of the present invention is to provide an improved process for the conversion of primary alcohols to fatty acids. A still further object of the present invention is to provide an improved process for the conversion of vicinal-diols to fatty acids. Yet another object of the present invention is to provide an improved process for the conversion of alcohols to fatty acids in the presence of a ruthenium catalyst and a peracid oxidizing agent. Yet another object of the present invention is to provide an improved process for the conversion of certain alcohols to fatty acids in the presence of a ruthenium catalyst, an oxidizing agent and an inert organic solvent. Another and further object of the present invention is to provide an improved process for the conversion of primary alcohols and vicinal-diols to fatty acids in the presence of a ruthenium catalyst, a peracid oxidizing agent, an inert organic solvent and an organic or inorganic base.

SUMMARY OF THE INVENTION

A process for the preparation of fatty acids by the oxidation of primary alcohols and vicinal-diols comprising, contacting the particular alcohol with a ruthenium catalyst and a peracid oxidizing agent. If desired the process may include the addition of a small amount of an organic or inorganic base. An inert organic solvent may be utilized and the reaction may then be carried out as the reflux temperature of the solvent.

DETAILED DESCRIPTION OF THE INVENTION

Suitable alcohols for use in accordance with the present invention include primary alpha-alcohols, such as butanol-1, hexanol-1, octanol-1, decanol-1, etc., and vicinal-diols, such as, octane-1, 2-diol, cyclohexane-1, 2-diol, etc. Preferred primary and vicinal alcohols are the aliphatic alcohols having 2 to 20 carbon atoms and most preferred are aliphatic alcohols of 4 to 12 carbon atoms as well as cycloaliphatic diols of 5 to 7 carbon atoms.

Where the term "peracid" is utilized in accordance with the present invention, this term is meant to include materials as defined in "The Condensed Chemical Dictionary", 6th Edition, Reinhold and Company, 1956. In accordance with this definition, peracids are derivatives of hydrogen peroxide, the molecules of which contain one or more directly linked pairs of oxygen atoms, O-O-. These peracids do not include permanganic, perchloric, and periodic acids. Suitable peracids for use in accordance with the present invention are peracetic, performic, perphthalic, persuccinic, persulfuric, perboric, pertrichloroacetic, pertrifluoroacetic, perbenzoic, n-chloro-benzoic, p-nitrobenzoic, etc.

The oxidizing agent should be used in an amount sufficient to obtain complete oxidation of the alcohols to fatty acids. Specifically, the oxidizing agent should be present in an amount sufficient to supply between about 0.9 and 3.2 mole equivalents of oxygen per mole of alcohol.

The catalyst utilized in accordance with the present invention is ruthenium metal or an organic or inorganic ruthenium compound. Any organic or inorganic ruthenium salt having an anion which does not unduly retard the formation of the desired products by an extraneous side reaction can be utilized as a catalyst. Salts of fatty acids having up to about four carbon atoms, such as, ruthenium formate, acetate, propionate or butyrate, are preferred organic salts. Inorganic salts in general and simple inorganic salts in particular constitute a highly preferred class of ruthenium-containing catalysts. Examples of useful inorganic salts are ruthenium trichloride, ruthenium tribromide, ruthenium sulfide, ruthenium carbonate and the like. Ruthenium halides and ruthenium dioxide are particularly useful inorganic salts. In addition to the above, organo-metallic compounds, such as, bis (cyclopentadienyl) ruthenium and ruthenium carbonyls, such as Ru $(CO)_5$, $Ru_2$ $(CO)_9$, [Re $(CO)_4]_3$, Ru (CO) X, wherein X is chlorine, bromine or iodine, may also be employed as catalysts. A wide variety of ruthenium chelates are also applicable in the present process. Preferred chelates have a donor atom selected from the group consisting of group V-B and group VI-B elements of the Periodic Table. More preferred chelating agents have a donor atom selected from the class consisting of nitrogen and oxygen. Tri-amines, tetra-amines and oximes comprise a preferred class of chelating agents having nitrogen as a donor atom. Dibasic carboxylic acids comprise a preferred class of chelating agents having oxygen as a donor atom. Thus, chelates derived from well-known chelating agents, such as salicylic acid, -acyloin oxime, -benzoin oxime, dimethylglyoxime, acetylacetone, aminoacetic acid, oxalic acid, diethylenetriamine, triethylenetetraamine, malonic acid, and the like can be employed. Illustrative examples of such chelates include $Na_3[Re(C_2O_4)_3]$ $6H_2O$, $K_3[Ru-(malonate)3]$ $5H_2O$, tris (ethylene diamine) ruthenium, and the like.

The catalyst should be present in amounts between about 0.00001 and 1.0% by weight of the reaction mixture and, preferably, between about 0.0001 and 0.001% by weight.

Suitable solvents for use in accordance with the present invention include any inert solvent which is not susceptible to oxidation. Preferred solvents include solvents selected from the group consisting of paraffinic hydrocarbons, and halogenated hydrocarbons, such as, hexane, heptane, chloroform, carbon tetrachloride, etc. Such solvents should have a boiling range between about 40° and 100° C. In the event that the peracid or the catalyst is not readily miscible with the solvent, agitation may be advantageously employed.

As previously indicated, the oxidation process reaction mixture may include a small amount of an organic or inorganic base which is added to the peracid oxidizing agent. Any organic or inorganic base which does not interfere with the main reaction is suitable. Organic bases, such as, primary, secondary, and tertiary organic amines are useful and particularly triethylamine and pyridine. Group IA and group IIA metal salts of fatty acids having up to about 4 carbon atoms such as sodium acetate are preferred. Inorganic bases, such as, group IA and group IIA metal hydroxides, carbonates, and phosphates are particularly preferred. The mole ratio of peracid to base can be from about 5 to 1 to 100 to 1. However, the preferred range is about 10 to 1 to 50 to 1 and still more particularly, between about 25 to 1 and 40 to 1.

The operation of the present invention is illustrated by the following examples:

EXAMPLE I

Octanol-1 (20 G.), $RuCl_3.1-3H_2O$(0.05 g.) and heptane (100 ml.) were placed in a 1 liter, three-neck flask equipped with an addition funnel, a thermometer, a mechanical stirrer and a reflux condenser. The reaction mixture was stirred to obtain a homogeneous solution of the ruthenium compound in the organic solvent. At this time, 100 g. of 40% by weight peracetic acid was added. An exothermic reaction took place. The peracid was added in such a way as to keep the mixture at a reflux temperature of about 82° C. After the addition of the peracid was completed, the reaction mixture was allowed to reflux for an additional hour and was then cooled to room temperature. The reaction mixture formed two phases which were then separated. The acidic phase was extracted with two portions of 100 ml. of heptane. The combined heptane fractions were washed with 100 ml. of water to secure complete elimination of the acetic acid. The heptane layer was then concentrated to a residue under reduced pressure. The residue was analyzed by gas chromatography for fatty acids and found to contain 0.9 g. of heptanoic acid and 18.0 g. of octanoic acid. Molar selectivity to total acids was found to be 85.7%.

EXAMPLE II

The experimental procedure of Example 1 was repeated except that 2.5 g. of sodium acetate trihydrate were added to the peracetic acid. In this particular run, an 88.4% molar selectivity to total acids was obtained.

These runs plus additional runs utilizing varying rate molar ratios of octanol-1 to peracetic acid are summarized in the following table.

TABLE I

| Run | 1 | 2 | 3 | 4 |
|---|---|---|---|---|
| Octanol-1, g. (mole) | 20, (0.154) | 20, (0.154) | 20, (0.154) | 20, (0.154) |
| $RuCl_3 . 1-3 H_2O$, g. | 0.05 | 0.05 | 0.05 | 0.05 |
| 40% AcOOH, g. (mole) | 100, (0526) | 100, (0526) | 59, (0.308) | 29.5 (0.154) |
| $AcONa . 3 H_2O$, g. b. | — | 2.5 | 1.5 | 0.75 |
| Heptane, ml. | 100 | 100 | 100 | 100 |
| Temp., ° C | 82 | 82 | 82 | 82 |
| Unreacted Octanol-1, g. | — | — | — | 5.6 |
| $C_7$ acid, g. | 0.9 | 0.9 | 0.7 | — |
| $C_8$ acid, g. | 18.0 | 18.6 | 17.3 | 7.4 |
| Octyl acetate, g. | 1.9 | — | — | — |
| Octyl aldehyde, g. | — | — | 1.9 | 5.0 |
| By-products, g | 2.3 | 1.5 | 1.4 | 0.9 |
| Total Acids, g. | 18.9 | 19.5 | 18.0 | 7.4 |
| Total products, g. | 23.1 | 21.0 | 21.4 | 19.0 |
| Conversion, % | 100 | 100 | 100 | 72.1 |
| Molar Selectivity to Total Acids, % | 85.7 | 88.4 | 81.5 | 46.0 a. | a. Molar selectivity to acid and aldehyde is 80.9%.
b. AcOOH is peracetic acid.

EXAMPLE III

Octane-1, 2-diol (1416 g.), $RuCl_3.1-3H_2O$(0.05 g.) and hexane (100 ml.) were added to the reaction flask of Example I. 77 g. of 40% peracetic acid were added and the reaction was conducted in the same manner as Example I. The reaction resulted in 100% conversion and a molar selectivity to total acids of 73%.

EXAMPLE IV

Cyclohexane-1, 2-diol (11.6 g.), $RuCl_3 \cdot 1\text{-}3H_2O$ (0.05 g.) and hexane (100 ml.) were added to the reactor of Example I. 100 g. of 40% peracetic acid were added and the reaction conducted as in Example I. This run resulted in a conversion of 81.5% and a molar selectivity to adipic acid of 80% was obtained.

EXAMPLE V

Example IV was repeated except that 2 g. of sodium acetate were added with the peracetic acid. 100% conversion was obtained with a molar selectivity to acids of 65%.

While specific materials and techniques have been disclosed herein and the process has been illustrated by specific examples, it is to be understood that those skilled in the art will readily recognize certain modifications and variations within the scope of the invention. Accordingly, the present invention is to be limited only in accordance with the appended Claims.

I claim:

1. A process for the production of fatty carboxylic acids which consists essentially of contacting primary aliphatic alcohols with a percarboxylic acid oxidizing agent, said percarboxylic acid providing between 0.9 mole and 3.2 mole equivalents of oxygen per mole of alcohol, in the presence of a ruthenium-containing catalyst selected from the group consisting of ruthenium metal, inorganic ruthenium salts and organic ruthenium salts and an inert solvent selected from the group consisting of hexane, heptane, chloroform and carbon tetrachloride said process being carried out at the reflux temperature of said solvent and recovering carboxylic acids from the reaction mixture.

2. A process in accordance with claim 1 wherein the alcohol is selected from the group consisting of butanol-1, hexanol-1, octanol-1, and decanol-1.

3. A process in accordance with claim 1 wherein a base of an alkali metal salt of a fatty acid is added to the reaction mixture.

4. A process in accordance with claim 1 wherein the alcohol has a boiling point below the boiling point of the solvent and the reaction is carried out at a pressure above atmospheric pressure.

5. A process in accordance with claim 1 wherein the percarboxylic acid oxidizing agent is selected from the group consisting of peracetic, performic, perphthalic, persuccinic, trichloroperacetic and trifluoroperacetic.

6. A process in accordance with claim 1 wherein the ruthenium-containing catalyst is ruthenium trichloride or ruthenium dioxide.

7. A process in accordance with claim 3 wherein the alkali metal salt is sodium acetate.

* * * * *